US00PP16990P2

(12) United States Plant Patent
Pieters

(10) Patent No.: US PP16,990 P2
(45) Date of Patent: Aug. 15, 2006

(54) ***CHRYSANTHEMUM* PLANT NAMED 'GEDI THREE LUCA'**

(50) Latin Name: *Chrysanthemum morifolium*
Varietal Denomination: Gedi Three Luca

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 17 days.

(21) Appl. No.: 11/116,912

(22) Filed: Apr. 27, 2005

(51) Int. Cl.
*A01H 5/00* (2006.01)

(52) U.S. Cl. ..... Plt./287

(58) Field of Classification Search ..... Plt./287
See application file for complete search history.

(56) References Cited

U.S. PATENT DOCUMENTS

PP13,796 P2 5/2003 Pieters
PP14,403 P2 12/2003 Pieters

*Primary Examiner*—Kent Bell
*Assistant Examiner*—Annette H Para
(74) *Attorney, Agent, or Firm*—Knobbe Martens Olson & Bear, LLP

(57) ABSTRACT

A new and distinct *Chrysanthemum* plant cultivar is disclosed, characterized by a flower that has a distinctive dark center. The plant produces a large number of flowers per stem, has a round, free-branching habit, and blooms consistently during the first two weeks of September.

1 Drawing Sheet

Figure 1:
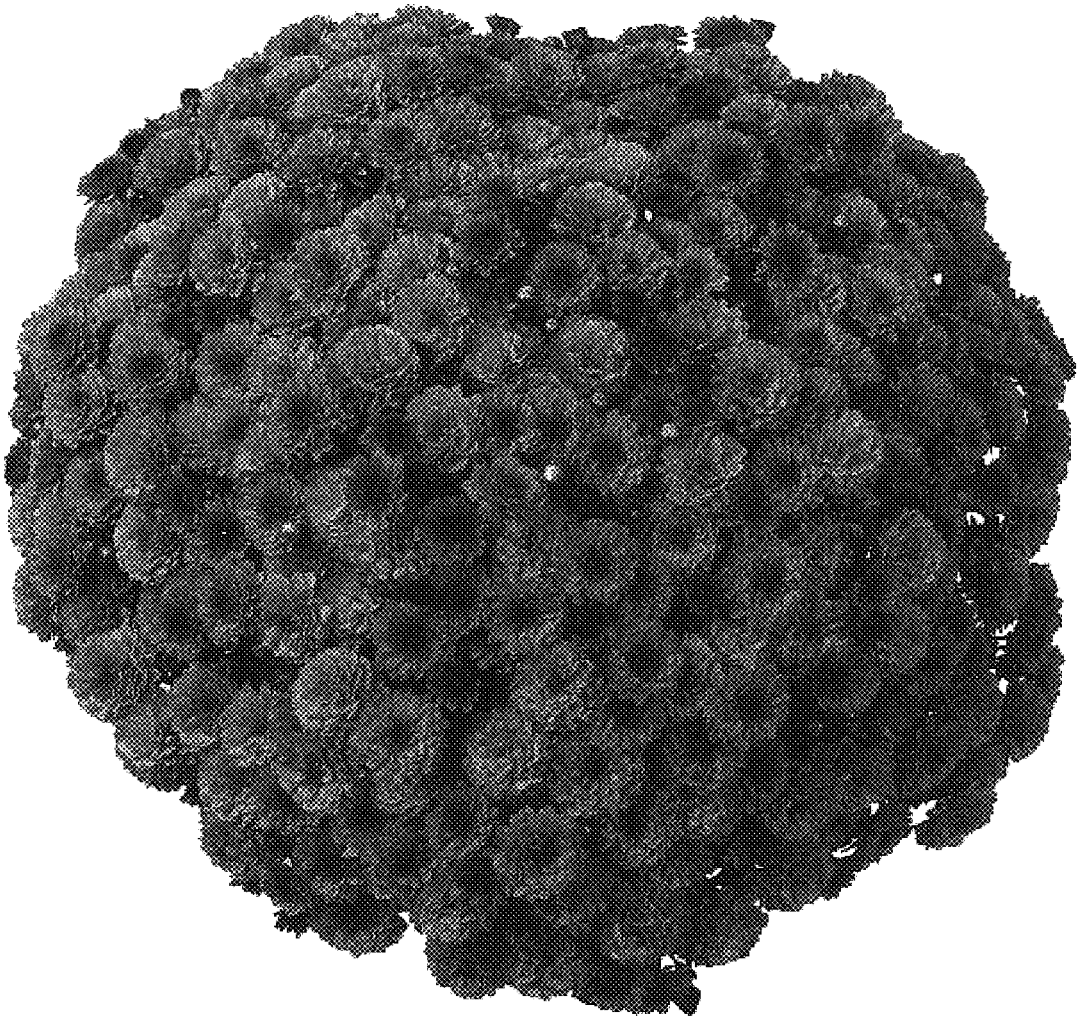

Latin name of the genus and species: *Chrysanthemum morifolium.*
Variety denomination: 'Gedi Three Luca'.

BACKGROUND OF THE INVENTION

The new cultivar 'Gedi Three Luca' is a product of the hybridization of an undistributed, unnamed, and unpatented female parent *Chrysanthemum* plant variety and a male parent *Chrysanthemum* plant variety '95 076-02' (unpatented, undistributed seedling), which was performed in September, 1999 in a controlled environment by Dirk Pieters. The new cultivar 'Gedi Three Luca' was first selected and asexually propagated in a controlled environment in Oostnieuwkerke, Belgium, by Dirk Pieters in September, 2002.

Asexual reproduction of the new cultivar 'Gedi Three Luca' by tissue culture and terminal cuttings was performed in Oxnard, Calif. and has shown that the unique features of this cultivar are stable and reproduced true to type on successive generations.

SUMMARY OF THE INVENTION

The cultivar 'Gedi Three Luca' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Gedi Three Luca'. These characteristics in combination distinguish 'Gedi Three Luca' as a new and distinct *Chrysanthemum* cultivar:

1. The flower has a distinctive dark center.
2. The plant blooms consistently during the first two weeks of September.

3. The plant produces a large number of flowers per stem.
4. The plant is free-branching, with a round plant habit.

Plants of the new cultivar 'Gedi Three Luca' are similar to plants of the unnamed, undistributed female parent variety in most horticultural characteristics, however plants of the new cultivar 'Gedi Three Luca' have a wider diameter flower with lighter colored ray florets than the plants of the female parent variety. Additionally, the new variety 'Gedi Three Luca' is more freely branching, and is shorter than the female parent variety.

Plants of the new cultivar 'Gedi Three Luca' are similar to plants of the male parent variety '95 076-02' in most horticultural characteristics, however plants of the new cultivar have darker ray florets and a longer lasting flower than plants of the male parent variety. Additionally, the new variety 'Gedi Three Luca' is taller and has a rounder growth habit than the plants of the male parent variety '95 076-02.'

In comparison to the commercially available variety 'Gedi One Nov' (U.S. Plant Pat. No. 13,796), 'Gedi Three Luca' has darker bronze-red ray florets and a smaller floral diameter. Additionally, the flower of the new variety 'Gedi Three Luca' has fewer ray florets than the comparable variety 'Gedi One Nov.' The new variety 'Gedi Three Luca' also has approximately 10 more flowers per stem than the comparable variety 'Gedi One Nov.'

In comparison to the commercially available variety 'Gedi Two Fig' (U.S. Plant Pat. No. 14,403), 'Gedi Three Luca' has more ray florets that are also a much darker bronze-red color. Additionally, the new variety 'Gedi Three Luca' has a larger diameter flower than does the comparable variety 'Gedi Two Fig.' Further, the flower of the new variety 'Gedi Three Luca' lasts about eight days longer than the flower of the comparable variety 'Gedi Two Fig.'

BRIEF DESCRIPTION OF THE PHOTOGRAPH

The accompanying photograph in FIG. 1 illustrates in full color a typical plant of 'Gedi Three Luca' grown in a 2 gallon container. One cutting was used in the pot. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'Gedi Three Luca' plants grown in Oxnard, Ventura County, Calif., during the month of September, 2003. The growing temperature ranged from about 12° C. to 15° C. at night to about 12° C. to 20° C. during the day. Measurements and numerical values represent averages of typical flowering types, and are believed to apply to plants of the variety grown under similar conditions of soil and climate elsewhere:

Botanical classification: *Chrysanthemum morifolium* 'Gedi Three Luca.'
Commercial classification: Garden-type *Chrysanthemum*.

PROPAGATION

Time to rooting: 7 to 14 days at approximately 21° C.
Root description: Fine, fibrous.

PLANT

Growth habit: Mounding herbaceous perennial.
Height: Approximately 29.5 cm.
Plant spread: Approximately 32 cm.
Growth rate: Moderate.
Branching characteristics: Free branching.
Length of lateral branches: Approximately 24 cm.
Number of leaves per lateral branch: Approximately 18.
Age of plant described: Approximately 140 days from a rooted cutting.

FOLIAGE

Leaf:
- *Arrangement.*—Alternate.
- *Average length.*—Approximately 6.2 cm.
- *Average width.*—Approximately 4.9 cm.
- *Shape of blade.*—Ovate.
- *Apex.*—Cuspidate.
- *Base.*—Attenuate.
- *Attachment.*—Stalked.
- *Margin.*—Palmately lobed and toothed.
- *Texture of top surface.*—Lightly pubescent.
- *Texture of bottom surface.*—Lightly pubescent.
- *Leaf internode length.*—Approximately 1.9 cm.
- *Color.*—Young foliage upper side: Near Green 137A. Young foliage under side: Near Green 137B. Mature foliage upper side: Near Green 137A. Mature foliage under side: Near Green 137A.
- *Venation.*—Type: Palmately net. Venation color upper side: Near Green 138A. Venation color under side: Near Green 138B.

Petiole:
- *Average length.*—Approximately 2.3 cm.
- *Color.*—Near Green 137B.
- *Diameter.*—Approximately 0.2 cm.

BLOOM

Flower:
- *Flowering habit.*—Induced by darkness period greater than approximately 13.5 hours, approximately 45 days of appropriate day length required to induce and develop blooms.
- *Flower form.*—Decorative.
- *Natural flowering season.*—Approximately the first two weeks of September.
- *Number of flowers per lateral branch.*—Approximately 24.
- *Diameter.*—Approximately 5.1 cm.
- *Depth.*—Approximately 2.9 cm.
- *Longevity on plant.*—Approximately 29 days.
- *Persistence.*—Persistent.

Ray florets:
- *Appearance.*—Matte.
- *Texture.*—Smooth.
- *Average number of ray florets per flower.*—Approximately 200.
- *Shape.*—Oblong.
- *Aspect.*—Flat.
- *Margin.*—Entire.
- *Apex.*—Retuse.
- *Length.*—Approximately 2.8 cm.
- *Width.*—Approximately 0.9 cm.
- *Color.*—Upper surface at first opening: Near Greyed-red 178A. Upper surface at maturity: Near Greyed-orange 171B. Upper surface at fading: Near Greyed-orange 168C. Under surface at first opening: Near Greyed-red 180A. Under surface at maturity: Near Greyed-orange 171B. Under surface at fading: Near Greyed-orange 167D.

Disc florets:
- *Appearance.*—Shiny.
- *Texture.*—Smooth.
- *Average number of disc florets per disc.*—Approximately 20.
- *Shape.*—Cylindric.
- *Apex.*—Obtuse.
- *Average length.*—Approximately 0.6 cm.
- *Average width.*—Approximately 0.1 cm.
- *Color.*—At first opening: Near Yellow 7A. At maturity: Near Yellow 4C. At fading: Near Orange 26A.

Peduncle:
- *Length.*—At terminal end (shortest): Approximately 3.6 cm. At lateral end (longest): Approximately 7.1 cm.
- *Angle to stem.*—Acute.
- *Strength.*—Moderate.
- *Color.*—Near Green 137A.
- *Habit.*—Upright.
- *Diameter.*—Approximately 0.2 cm.
- *Surface texture.*—Lightly pubescent.

Flower bud:
- *Length.*—Approximately 9 cm.
- *Diameter.*—Approximately 0.8 cm.
- *Form.*—Globular.
- *Color.*—Near Greyed-red 181A.

Involucral bracts (Phyllaries):
- *Appearance.*—Matte.
- *Texture.*—Lightly pubescent.
- *Number.*—Approximately 36.
- *Shape.*—Oblanceolate.
- *Margin.*—Entire.
- *Apex.*—Acute.
- *Length.*—Approximately 0.9 cm.
- *Width.*—Approximately 0.8 cm.

*Color.*—Upper side: Near Green 137A. Under side: Near Green 137A.

REPRODUCTIVE ORGANS

Ray florets:
*Number of pistils per floret.*—1.
*Stigma shape.*—2 branched.
*Stigma color.*—Near Yellow 13A.
*Style color.*—Near Yellow 2A.
*Style length.*—Approximately 0.8 cm.
*Stamens.*—Absent.

Disc florets:
*Number of pistils per floret.*—1.
*Stigma shape.*—Two-branched.
*Stigma color.*—Near Yellow 4C.
*Style length.*—Approximately 0.3 cm.
*Style color.*—Near Yellow-green 154D.
*Number of stamens per floret.*—5.
*Anther shape.*—Tubular.
*Anther color.*—Near Yellow 7B.
*Pollen color.*—Near Yellow 7B.

OTHER CHARACTERISTICS

Disease resistance: Neither resistance nor susceptibility to diseases or pests has been observed in this variety.

Drought tolerance/cold tolerance: Flowering plants are hardy to low temperature about −2° C. Non-flowering plants are hardy in the approximate range of 3° C. to −6° C., depending upon duration of cold an amount of moisture in the soil. With adequate water plants are hardy to a high temperature of 45° C.

Fruit/seed production: Commercially, this plant is not used or observed in a stage wherein seeds would be produced. Therefore, seed production has not been observed.

What is claimed is:

1. A new and distinct cultivar of *Chrysanthemum* plant named 'Gedi Three Luca' as herein illustrated and described.

* * * * *